(12) United States Patent
Kojima (10) Patent No.: US 8,139,712 B2
(45) Date of Patent: Mar. 20, 2012

(54) RADIATION IMAGING APPARATUS AND METHOD FOR BREAST

(75) Inventor: Tetsuya Kojima, Kaisei-machi (JP)

(73) Assignee: Fujifilm Corporation (JP)

( * ) Notice: Subject to any disclaimer, the term of this patent is extended or adjusted under 35 U.S.C. 154(b) by 79 days.

(21) Appl. No.: 12/559,116

(22) Filed: Sep. 14, 2009

(65) Prior Publication Data

US 2010/0067648 A1 Mar. 18, 2010

(30) Foreign Application Priority Data

Sep. 17, 2008 (JP) ................................. 2008-238147

(51) Int. Cl.
*A61B 6/04* (2006.01)
*H05G 1/58* (2006.01)
*H05G 1/02* (2006.01)

(52) U.S. Cl. ......................... 378/37; 378/98.8; 378/116

(58) Field of Classification Search ................ 378/4–20, 378/41, 42, 44–46, 51, 53, 62, 91, 98, 98.8, 378/98.9, 114–116, 204, 210
See application file for complete search history.

(56) References Cited

U.S. PATENT DOCUMENTS

| | | | |
|---|---|---|---|
| 6,480,565 B1 | 11/2002 | Ning | |
| 6,928,314 B1* | 8/2005 | Johnson et al. | 600/407 |
| 7,689,042 B2* | 3/2010 | Brunner et al. | 382/199 |
| 7,702,142 B2* | 4/2010 | Ren et al. | 382/131 |
| 7,881,428 B2* | 2/2011 | Jing et al. | 378/37 |
| 2004/0081273 A1* | 4/2004 | Ning | 378/37 |
| 2005/0113681 A1* | 5/2005 | DeFreitas et al. | 600/426 |
| 2009/0003518 A1* | 1/2009 | Sadakane et al. | 378/19 |
| 2009/0034684 A1* | 2/2009 | Bernard et al. | 378/98 |
| 2009/0080604 A1* | 3/2009 | Shores et al. | 378/37 |
| 2009/0082660 A1* | 3/2009 | Rahn et al. | 600/411 |

* cited by examiner

*Primary Examiner* — Anastasia Midkiff
(74) *Attorney, Agent, or Firm* — Studebaker & Brackett PC; Donald R. Studebaker (57) ABSTRACT

A radiation imaging apparatus in which early recognition of breast cancer can be made possible by acquiring both a radiation tomographic image that accurately displays a tumor mass and a radiation planar image that accurately displays calcification. The apparatus includes an image processing unit for generating a tomographic image signal in a first imaging mode and generating a planar image signal in a second imaging mode, a computing unit for computing an imaging direction for obtaining a radiation planar image based on a location designated in a radiation tomographic image, and a control unit for controlling a rotational driving device and a radiation generating unit to obtain the radiation tomographic image in the first imaging mode, and controlling the rotational driving device according to the computed imaging direction and controlling the radiation generating unit to obtain the radiation planar image in the second imaging mode.

11 Claims, 7 Drawing Sheets

RADIATION IMAGING APPARATUS AND METHOD FOR BREAST

CROSS-REFERENCE TO RELATED APPLICATION

The present application claims priority from Japanese Patent Application No. 2008-238147 filed on Sep. 17, 2008, the contents of which are incorporated herein by reference in their entirety.

BACKGROUND OF THE INVENTION

1. Field of the Invention

The present invention relates to a radiation imaging apparatus and method for obtaining a radiation tomographic image of a breast by computer tomography (CT) and a radiation planar image appropriately displaying a condition of calcification in a breast.

2. Description of a Related Art

Conventionally, breast cancer examinations have been made by using palpation and ultrasonic diagnoses. However, in these examinations, only cancer cells that have been grown to some degree can be easily found. Accordingly, mammography for obtaining X-ray images, in which tumor masses and calcification produced in early breast cancer are relatively easily found, is used in combination. However, X-ray images obtained in mammography are simple planar images, and therefore, when the tumor mass part or the calcified part as a target of examination overlaps with tissues such as mammary gland, detection of a focus is difficult.

Accordingly, a radiation tomographic imaging apparatus for breast (mammography CT apparatus) using computer tomography (CT) that can obtain three-dimensional (3D) images has been developed. Even when a focus part overlaps with a radiopaque part, the mammography CT apparatus can make an accurate evaluation and has effect on early recognition of breast cancer.

As an example of a mammography CT apparatus, U.S. Pat. No. 6,480,565 B1 discloses a device for producing a three-dimensional tomographic mammography image of a breast of a patient. The device disclosed in U.S. Pat. No. 6,480,565 B1 comprises: a gantry frame; at least one motor for moving the gantry frame to form a data acquisition geometry; a source of radiation attached to the gantry frame to move with the gantry frame; a flat panel detector attached to the gantry frame to move with the gantry frame, the flat panel detector being disposed in a path of the radiation; and a support on which the patient rests while the mammography projection images are taken, the support supporting the patient such that the breast is disposed between the source of radiation and the flat panel detector; the support comprising a table on which the patient lies while the mammography projection images are taken; wherein the at least one motor moves the gantry frame so that the flat panel detector takes a volume scan of the breast; and wherein the table has two breast holes for both of the patient's breasts.

When breast cancer detection is performed by using the device disclosed in U.S. Pat. No. 6,480,565 B1, the patient rests face down on the table to allow two breasts to extend through the two breast holes, and one breast descends between the radiation source and the flat panel detector. The radiation source and the flat panel detector perform radiation imaging at each predetermined angular position while rotating together around a rotational axis, and thereby, the flat panel detector obtains radiation images of the breast in plural directions. The image signals obtained by the flat panel detector are transmitted to an image reconstruction and processing module. The image reconstruction and processing module three-dimensionally reconstructs the obtained radiation images to create a radiation tomographic image of the breast. Since the radiation tomographic image of the breast is a 3D image, a focus part at the rear side of the tissues such as mammary gland can be detected.

Since small tumor masses and calcification play an important part for early recognition in breast cancer examinations, it is important to sufficiently image them. In a radiation planar image obtained by the mammography apparatus, a calcified part exhibits image absorption equal to a bone, and a relatively small calcified part can be easily visualized. On the other hand, in a radiation tomographic image obtained by the mammography CT apparatus, a tumor mass can be detected, but detectability is not high for fine calcification because high-frequency information is deteriorated when the radiation tomographic image is created by reconstructing the plural radiation images.

Accordingly, it is conceivable that the tumor mass is detected in the radiation tomographic image and the fine calcified part is detected in individual radiation images. However, when obtaining plural radiation images to be used for creating the radiation tomographic image in the mammography CT apparatus, an extremely large number of times of imaging for obtaining three hundred images per one rotation, for example, are necessary. Therefore, in order to suppress the damage by the large number of times of exposure, radiation with low energy and low dose is selected to form a radiation cone beam to be used for production of radiation tomographic image. Accordingly, if radiation images obtained in the middle of formation of a radiation tomographic image in the mammography CT apparatus are singly used, fine calcification cannot sufficiently be detected in the individual images.

SUMMARY OF THE INVENTION

The present invention has been achieved in view of the above-mentioned points. A purpose of the present invention is to provide a radiation imaging apparatus and method in which early recognition of breast cancer can be made possible by acquiring both a radiation tomographic image that accurately displays a tumor mass and a radiation planar image that accurately displays calcification.

In order to solve the above-mentioned problem, a radiation imaging apparatus according to one aspect of the present invention includes: a table formed with an opening for allowing a breast of an examinee to pass through when the examinee lies down on the table; a radiation generating unit for applying a radiation beam to the breast passing through the opening of the table; a radiation detecting unit for detecting the radiation beam applied by the radiation generating unit and transmitted through the breast to output detection signals; a supporting plate for supporting the radiation generating unit and the radiation detecting unit such that the radiation generating unit and the radiation detecting unit are positioned to face each other with a rotational axis in between, the rotational axis being substantially orthogonal to the table and passing through the opening; a rotational driving device for rotating the supporting plate around the rotational axis; image processing means for generating image signals representing a predetermined number of radiation images based on the detection signals outputted from the radiation detecting unit and generating a tomographic image signal representing a radiation tomographic image by reconstructing the predetermined number of radiation images in a first imaging mode for obtaining the radiation tomographic image, and for generating a planar image signal representing a radiation planar image based on the detection signals outputted from the radiation detecting unit in a second imaging mode for obtaining the radiation planar image; computing means for computing an imaging direction for obtaining the radiation planar image in the second imaging mode based on a location designated in the radiation tomographic image obtained in the first imaging mode; control means for controlling the rotational driving device and the radiation generating unit to perform imaging for obtaining the radiation tomographic image in the first imaging mode, and controlling the rotational driving device according to the imaging direction computed by the computing means and controlling the radiation generating unit to perform imaging for obtaining the radiation planar image in the second imaging mode; and an image display unit for selectively displaying at least one of the radiation tomographic image obtained in the first imaging mode and the radiation planar image obtained in the second imaging mode.

Further, a radiation imaging method according to one aspect of the present invention is a radiation imaging method to be used in a radiation imaging apparatus including a table formed with an opening for allowing a breast of an examinee to pass through when the examinee lies down on the table, a radiation generating unit for applying a radiation beam to the breast passing through the opening of the table, a radiation detecting unit for detecting the radiation beam applied by the radiation generating unit and transmitted through the breast to output detection signals, a supporting plate for supporting the radiation generating unit and the radiation detecting unit such that the radiation generating unit and the radiation detecting unit are positioned to face each other with a rotational axis in between, the rotational axis being substantially orthogonal to the table and passing through the opening, and a rotational driving device for rotating the supporting plate around the rotational axis, and the method includes the steps of: (a) controlling the rotational driving device and the radiation generating unit to perform imaging for obtaining a radiation tomographic image; (b) generating image signals representing a predetermined number of radiation images based on the detection signals outputted from the radiation detecting unit, and generating a tomographic image signal representing a radiation tomographic image by reconstructing the predetermined number of radiation images; (c) computing an imaging direction for obtaining a radiation planar image based on a location designated in the radiation tomographic image obtained at step (b); (d) controlling the rotational driving device according to the imaging direction computed at step (c) and controlling the radiation generating unit to perform imaging for obtaining the radiation planar image; (e) generating a planar image signal representing the radiation planar image based on the detection signals outputted from the radiation detecting unit; and (f) selectively displaying at least one of the radiation tomographic image obtained at step (b) and the radiation planar image obtained at step (e).

According to the one aspect of the present invention, the radiation tomographic image is created by reconstructing the predetermined number of radiation images obtained by scanning the breast in the first imaging mode, and the imaging direction for obtaining the radiation planar image is computed based on the location designated in the radiation tomographic image, and then, the radiation planar image is obtained along the computed imaging direction in the second imaging mode. Thereby, both the radiation tomographic image that accurately displays a tumor mass and the radiation planar image that accurately displays calcification are obtained, and early recognition of breast cancer can be made possible.

DESCRIPTION OF THE PREFERRED EMBODIMENTS

Hereinafter, preferred embodiments of the present invention will be explained in detail with reference to the drawings. The same reference numbers are assigned to the same component elements and the description thereof will be omitted. In the following embodiments, the case where an X-ray is used as radiation will be explained, however, the present invention can be applied to cases of using $\alpha$-ray, $\beta$-ray, $\gamma$-ray, electron ray, ultraviolet ray, or the like.

Figure 1:
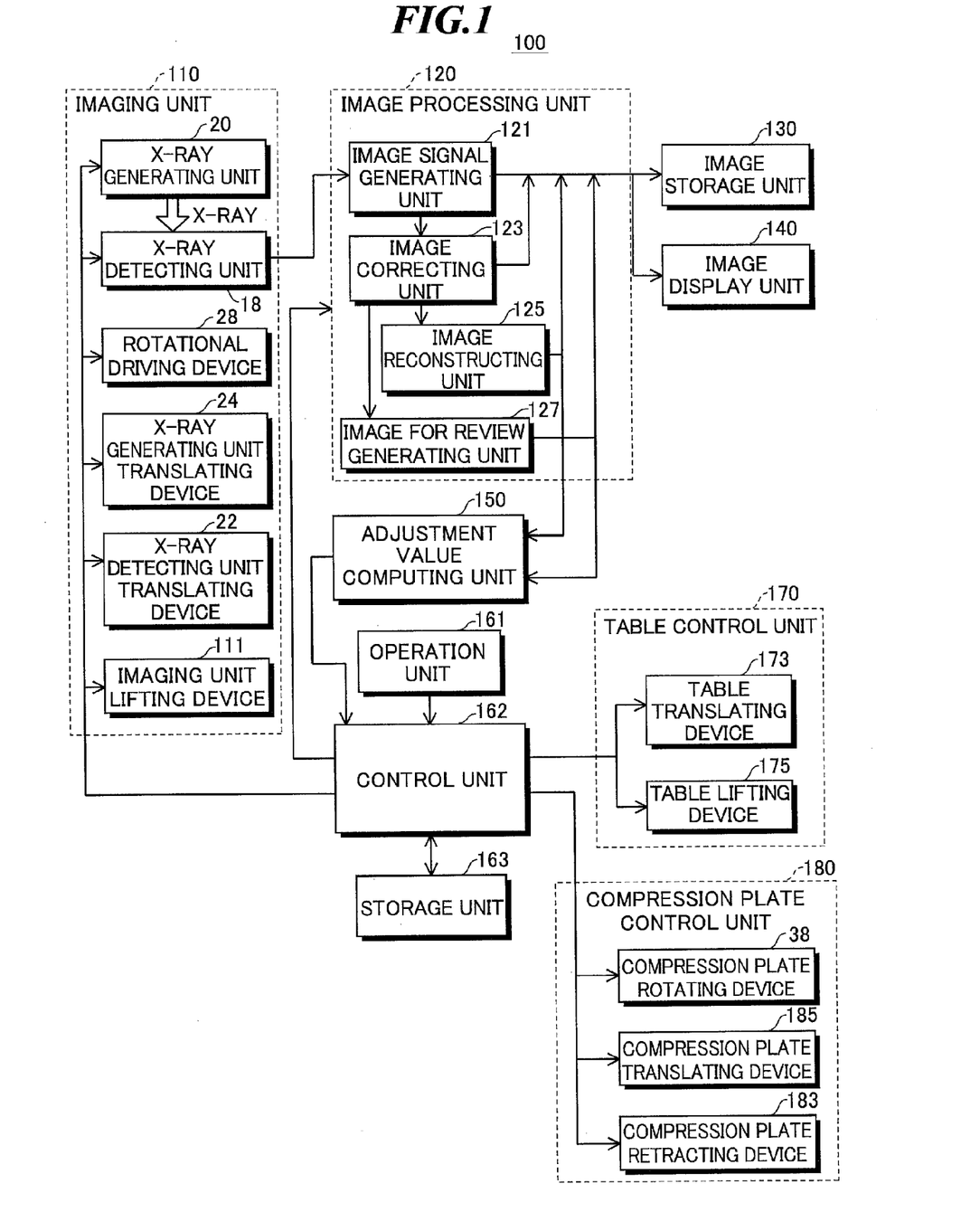
FIG. 1 is a block diagram showing a configuration of a radiation imaging apparatus according to one embodiment of the present invention.

FIG. 1 is a block diagram showing a configuration of a radiation imaging apparatus according to one embodiment of the present invention. The radiation imaging apparatus 100 includes an imaging unit 110, an image processing unit 120, an image storage unit 130, an image display unit 140, an adjustment value computing unit 150, an operation unit 161, a control unit 162, a storage unit 163, a table control unit 170, and a compression plate control unit 180.

The radiation imaging apparatus 100 obtains an X-ray tomographic image of an object to be inspected in a first imaging mode, and obtains an X-ray planar image of the object in an imaging direction determined based on the X-ray tomographic image in a second imaging mode.

The imaging unit 110 includes an X-ray generating unit 20, an X-ray detecting unit 18, a rotational driving device 28, an X-ray generating unit translating device 24, an X-ray detecting unit translating device 22, and an imaging unit lifting device 111.

When receiving a trigger signal from the control unit 162, the X-ray generating unit 20 radiates an X-ray beam. The X-ray detecting unit 18 has a flat panel display (FPD), on a surface of which plural X-ray detecting elements are arranged, and two-dimensionally detects the X-ray beam transmitted through a breast as the object to output detection signals to the image processing unit 120.

The image processing unit 120 includes an image signal generating unit 121, an image correcting unit 123, an image reconstructing unit 125, and an image for review generating unit 127.

The image signal generating unit 121 generates image signals representing X-ray transmission images (also simply referred to as "X-ray images") detected by the X-ray detecting unit 18 based on the detection signals received from the imaging unit 110. The image signals are outputted to the image correcting unit 123, the image storage unit 130, and the image display unit 140, and can be referred as obtained image information.

The image correcting unit 123 performs correction processing such as removing noise and reducing artifacts on the received image signals, and outputs the corrected image signals to the image reconstructing unit 125, the image for review generating unit 127, the image storage unit 130, and the image display unit 140.

When image signals representing a predetermined number of X-ray images obtained in plural directions with respect to the object are prepared in the first imaging mode, the image reconstructing unit 125 performs reconstruction computation on the image signals to generate a tomographic image signal representing a three-dimensional (3D) X-ray tomographic image of the object, and outputs the tomographic image signal to the image storage unit 130, the image display unit 140, and the adjustment value computing unit 150.

In the first imaging mode, the image display unit 140 displays the X-ray tomographic image based on the tomographic image signal outputted from the image reconstructing unit 125. Information of the X-ray tomographic image is used for discovering and locating tumor masses and calcification.

The image for review generating unit 127 generates an image for review signal representing an image for review to be used for adjustment of the radiation imaging apparatus 100, and supplies the image for review signal to the image storage unit 130, the image display unit 140, and the adjustment value computing unit 150. In the image for review, a scale is superimposed on the X-ray image or otherwise, and the image of the object within a screen is easily located.

The image storage unit 130 includes an image memory and/or a hard disk, and stores various kinds of image signals. If image information is necessary, the image signals can easily be read out and utilized.

The image display unit 140 selectively displays at least one of the X-ray tomographic image and the X-ray planar image of a breast to be used for confirming whether a tumor mass, calcification, cancer tissue, or the like exists within the breast or not in the examination of breast cancer. Further, the image display unit 140 displays the image for review to be used for monitoring and adjusting troubles and malfunctions of the radiation imaging apparatus 100. Specifically, in the case where an operator manually makes adjustment, it is necessary to make adjustment while observing the image for review displayed on the image display unit 140. Therefore, it is preferable that the image for review generating unit 127 inserts a scale into the display screen and generates an image for review, in which a numerical value indicating a deviation from a target value is indicated, for assisting the determination by the operator.

The adjustment value computing unit 150 checks conditions related to the adjustment value of the radiation imaging apparatus 100 as to whether accurate alignment has been made or not, whether correct resolving power has been obtained or not, whether unwanted noise is included or not, and so on based on the image for review signal. Further, the adjustment value computing unit 150 computes adjustment values necessary for eliminating the deviation from the target values with respect to the position of the screen frame, signal intensity, and other property values based on the image for review signal, and supplies the adjustment values to the control unit 162. The control unit 162 controls the imaging unit 110 and the table control unit 170 based on the adjustment values, and thereby, adjusts an amount of X-ray applied from the X-ray generating unit 20, directions and positions of the X-ray generating unit 20 and the X-ray detecting unit 18, and a position of the table 12 (FIG. 2), and so on.

Further, the adjustment value computing unit 150 computes adjustment values representing the imaging direction suitable for observation of the focus in the second imaging mode, that is, rotational positions of the X-ray generating unit 20 and the X-ray detecting unit 18 based on the information of the X-ray tomographic image obtained in the first imaging mode while referring to predetermined criteria, and supplies the adjustment values to the control unit 162. The control unit 162 controls the imaging unit 110, the table control unit 170, and the compression plate control unit 180 based on the adjustment values, and thereby, positions the X-ray generating unit 20 and the X-ray detecting unit 18 in the imaging direction represented by the adjustment values and adjusts the direction and position of a pair of compression plates 30 and 32 (FIG. 2) for compressing the object (breast of the examinee).

In the second imaging mode, X-ray imaging is performed in the imaging direction represented by the adjustment values computed by the adjustment value computing unit 150. The image display unit 140 displays an X-ray planar image based on the image signal (also referred to as "planar image signal" because the image signal is especially used for displaying an X-ray planar image) outputted from the image correcting unit 123.

The operation unit 161 includes a data input device such as a keyboard, a touch panel, and/or a mouse, and used when the operator inputs commands or information to the radiation imaging apparatus 100. The operation unit 161 may be used for manual designation of the locations of tumor masses and calcification in the X-ray tomographic image. Alternatively, the adjustment values, including ones related to the directions and positions of the X-ray generating unit 20 and the X-ray detecting unit 18, may be also directly designated by the operator operating the operation unit 161.

The control unit 162 controls the respective units of the radiation imaging apparatus according to the commands and adjustment values inputted by using the operation unit 161 and the adjustment values supplied from the adjustment value computing unit 150. When X-ray imaging is started, the control unit 162 drives the imaging unit 110 and generates control signals at each time the imaging procedure progresses, and thereby, controls the rotational driving device 28 for rotating a supporting plate for supporting the X-ray generating unit 20 and the X-ray detecting unit 18, and the imaging unit lifting device 111 for vertically moving a rotational shaft connected to the supporting plate. Thereby, the rotational driving device 28 and the imaging unit lifting device 111 adjust the directions and heights of the X-ray generating unit 20 and the X-ray detecting unit 18 to the set positions. Further, the control unit 162 controls the X-ray generating unit translating device 24 and the X-ray detecting unit translating device 22, and thereby, adjusts the distance between the X-ray detecting unit 18 and the object and the distance between the X-ray generating unit 20 and the object.

In the embodiment, the image processing unit 120, the adjustment value computing unit 150, and the control unit 162 are configured of a central processing unit (CPU) and software for allowing the CPU to execute various kinds of processing, however, they may be configured of digital circuits or analog circuits. The software (program) is stored in the storage unit 163. As a recording medium in the storage unit 163, not only the built-in hard disk but also a flexible disk, MO, MT, RAM, CD-ROM, DVD-ROM, or the like may be used.

The table control unit 170 includes a table translating device 173 for translating the table and a table lifting device 175 for vertically moving the table, and is controlled by the control unit 162. The position of the X-ray beam applied to the breast of the examinee can be easily adjusted by the vertical motion of the supporting plate for supporting the X-ray generating unit 20 and the X-ray detecting unit 18, or can be adjusted by changing the height of the table, on which the examinee is mounted, by moving up and down the table. Further, when the right and left breasts are switched for examination, it is necessary to relocate the new breast to the position of the rotational axis of the supporting plate at switching. Specifically, when two openings are formed in the table for the right and left breasts, the other opening can be translated to the position of the rotational axis for alignment.

The compression plate control unit 180 includes a compression plate rotating device 38 for rotating the compression plates, a compression plate translating device 185 for translating the compression plates, and a compression plate retracting device 183 for retracting the compression plates, and is controlled by the control unit 162. In the case where the compression plates are used when obtaining the X-ray planar image in the second imaging mode, the control unit 162 controls the compression plate control unit 180 according to the adjustment value received from the adjustment value computing unit 150 or operation unit 161. Thereby, the compression plate control unit 180 adjusts the direction and position of the compression plates. Note that use of the compression plate is arbitrary, and further, the direction and position of the compression plates may be manually adjusted.

Figure 2:
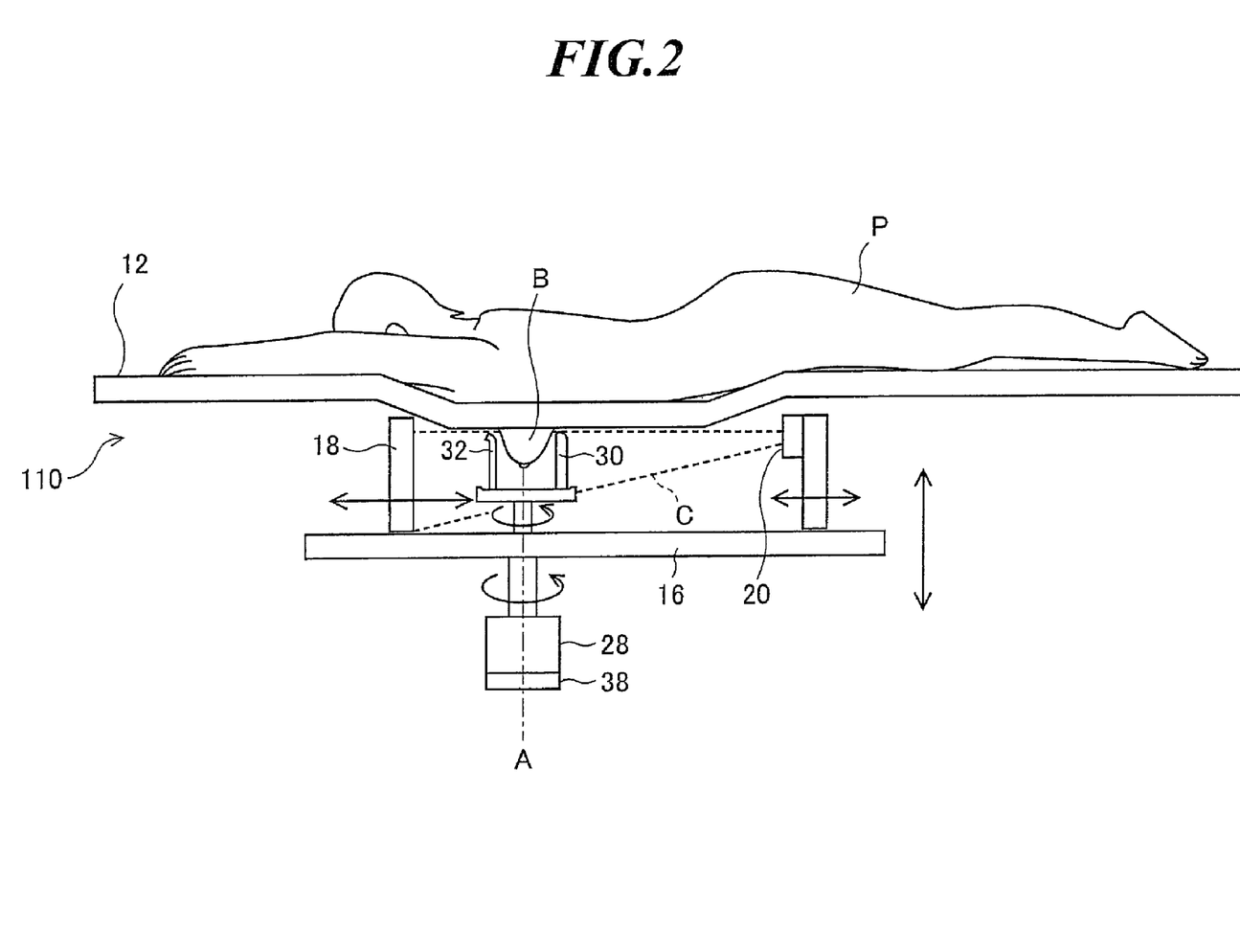
FIG. 2 is a side view showing an imaging unit of the radiation imaging apparatus according to one embodiment of the present invention.

FIG. 2 is a side view showing the imaging unit of the radiation imaging apparatus according to one embodiment of the present invention. As shown in FIG. 2, the imaging unit 110 includes the table 12 having an opening part in which an opening for passing breast "B" of examinee (patient) "P" is formed, the X-ray generating unit 20 for applying an X-ray beam (cone beam) "C" having a conical shape toward the breast "B" that has passed through the opening of the table 12, the X-ray detecting unit 18 for two-dimensionally detecting the intensity of incident X-ray beam applied by the X-ray generating unit 20 and transmitted through the breast "B", the supporting plate 16 on which the X-ray generating unit 20 and the X-ray detecting unit 18 are mounted, the rotational driving device 28 for rotating the supporting plate 16, and the compression plates 30 and 32 that may be used for compressing the breast "B" when an X-ray planar image is obtained in the second imaging mode.

The table 12 has an ergonomic shape suitable for allowing the breast "B" to project from the opening as much as possible when the examinee "P" lies down. Further, it is preferable that an opening diameter and a shape of the opening part can be selected according to the size of the breast "B". For example, the opening part is formed of a material such as a silicon resin that changes its shape according to the shape of the breast "B". Further, a part of the table 12 around the opening part is protruded below the other part and an X-ray shielding member is provided around the opening part, and thereby, the part of the examinee "P" other than the breast "B" is made difficult to be exposed to an X-ray. The X-ray beam "C" applied from the X-ray generator 20 is formed in a conical shape so as not to travel toward the examinee "P" lying down on the table 12.

The X-ray generating unit 20 uses an X-ray tube in which the wavelength or dose of an X-ray can be changed by changing at least one of a tube voltage, a target, and a filter. By appropriately adjusting them, optimum X-rays are generated in the first imaging mode for obtaining an X-ray tomographic image and the second imaging mode for obtaining an X-ray planar image, respectively. When the control unit 162 (FIG. 1) generates a control signal for selecting one of the X-ray generation condition adapted to the first imaging mode and the X-ray generation condition adapted to the second imaging mode, the X-ray generating unit 20 changes at least one of the tube voltage, target, and filter according to the control signal, and thereby, changes the wavelength or dose of an X-ray to be generated. For example, the X-ray dose used in the second imaging mode is made larger than the X-ray dose used in the first imaging mode, and thereby, a clear X-ray planar image can be obtained. On the other hand, in the first imaging mode of performing a large number of times of imaging, X-ray exposure can be suppressed.

As the X-ray detecting unit 18, it is desirable to use one in which pixel density can be changed. When an X-ray planar image is obtained in the second imaging mode, the pixel density is set higher than that when an X-ray tomographic image is obtained in the first imaging mode. Thereby, the X-ray planar image becomes finer, and grasp of the condition in the focus becomes easier. Further, enlarged display of the X-ray planar image becomes possible, and accurate observation of the condition of calcification, which is generally an extremely fine image, becomes easier. On the other hand, in the first imaging mode that takes time for generating the tomographic image signal, the computation time can be reduced.

The supporting plate 16 supports the X-ray generating unit 20 and the X-ray detecting unit 18 such that the X-ray generating unit 20 and the X-ray detecting unit 18 are positioned to face each other with the rotational axis "A" in between. The rotational axis "A" is substantially orthogonal to the table 12, and passes through the opening of the table 12. The rotational driving device 28 rotates the supporting plate 16 around the rotational axis "A". In FIG. 1, the compression plate rotating device 38 for rotating the compression plates 30 and 32 is also shown, and it will be explained later.

Figure 3:
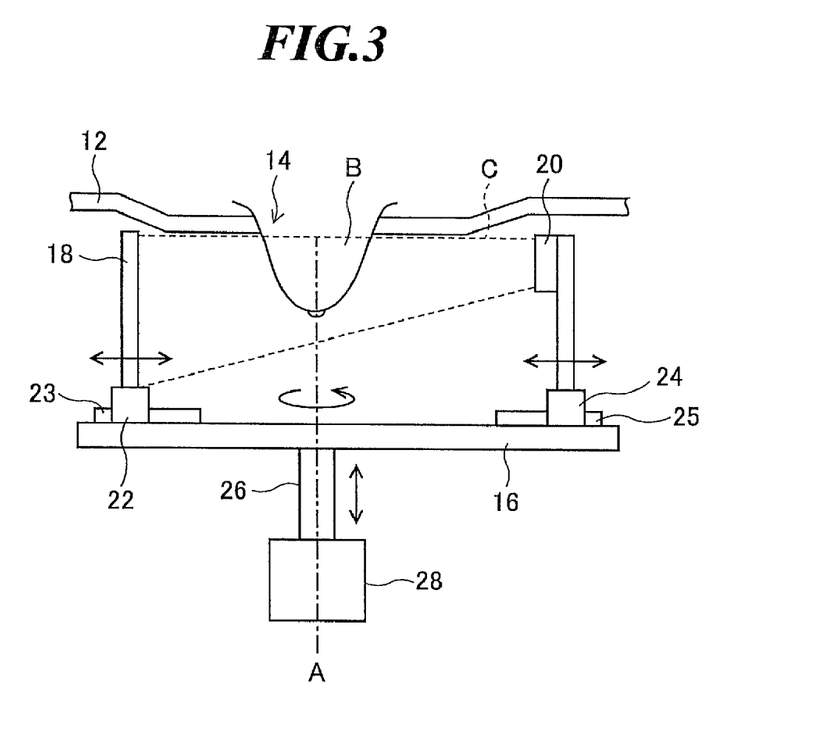
FIG. 3 is a side view showing a part of the imaging unit of the radiation imaging apparatus according to one embodiment of the present invention.
Figure 4:
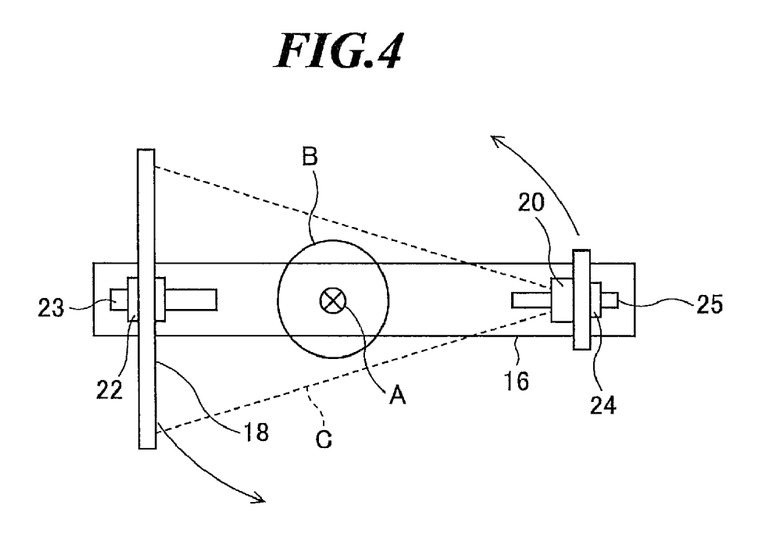
FIG. 4 is a plan view showing a part of the imaging unit of the radiation imaging apparatus according to one embodiment of the present invention.
Figure 5:
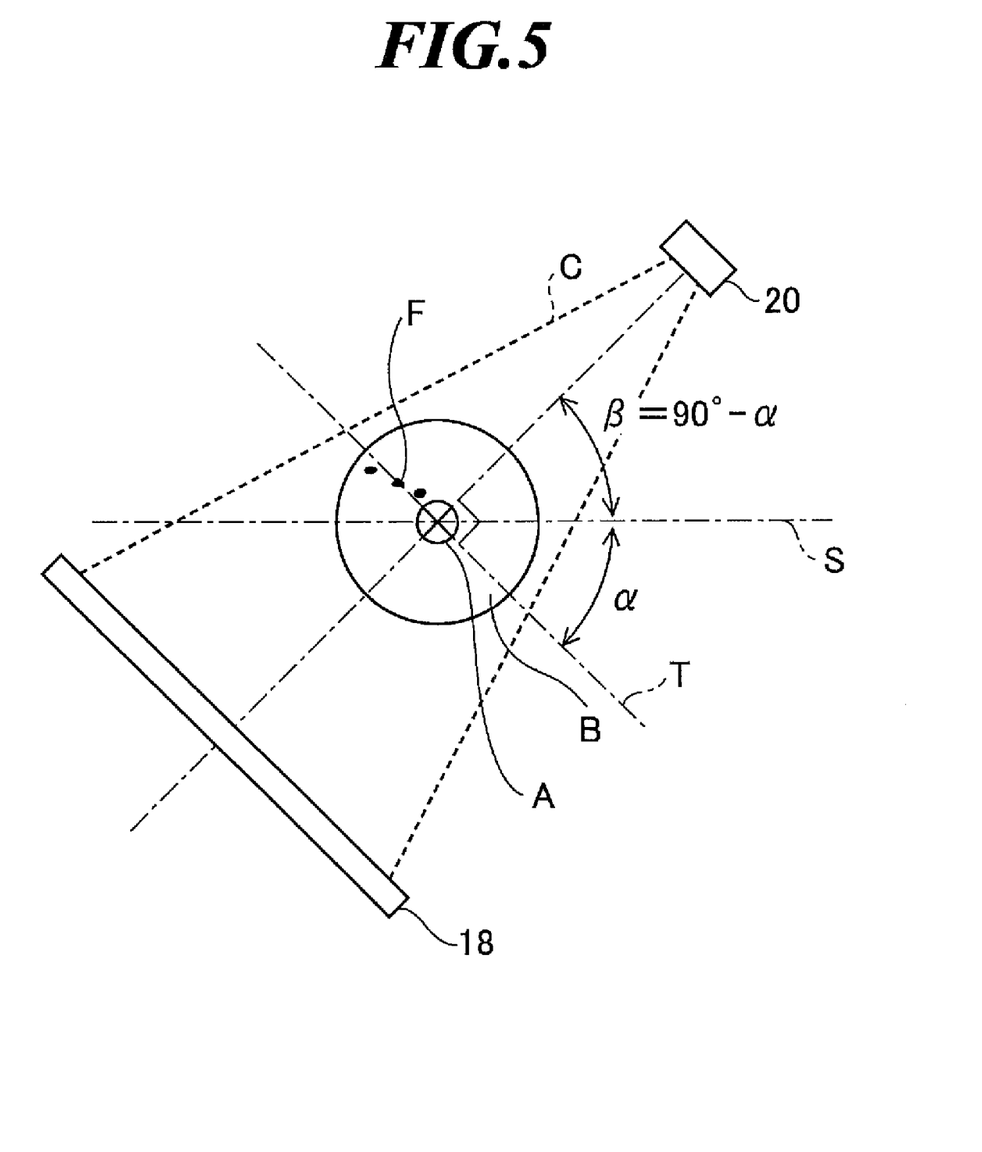
FIG. 5 is a plan view showing an arrangement example for acquiring an X-ray planar image in the imaging unit of the radiation imaging apparatus according to one embodiment of the present invention.

FIG. 3 is a side view showing a part of the imaging unit of the radiation imaging apparatus according to one embodiment of the present invention, FIG. 4 is a plan view showing a part of the imaging unit of the radiation imaging apparatus according to one embodiment of the present invention, and FIG. 5 is a plan view showing an arrangement example for acquiring an X-ray planar image in the imaging unit of the radiation imaging apparatus according to one embodiment of the present invention.

As shown in FIGS. 3 and 4, the X-ray generating unit 20 and the X-ray detecting unit 18 are mounted on the supporting plate 16, facing each other with the rotational axis "A" in between.

In the first imaging mode for obtaining an X-ray tomographic image, the rotational driving device 28 rotates the supporting plate 16 around the rotational axis "A", and thereby, the X-ray generating unit 20 and the X-ray detecting unit 18 rotate around the breast "B". The X-ray generating unit 20 applies an X-ray beam with predetermined timing, and the X-ray detecting unit 18 detects a predetermined number of X-ray images to output detection signals. The detection signals outputted from the X-ray detecting unit 18 are received by the image processing unit 120 (FIG. 1). The image processing unit 120 generates image signals representing the predetermined number of X-ray images, and reconstructs the predetermined number of X-ray images to create an X-ray tomographic image, and thereby, generates a tomographic image signal representing the X-ray tomographic image. Since it is necessary to obtain a number of X-ray images for creating an X-ray tomographic image, it is necessary that the X-ray beam applied from the X-ray generating unit 20 is an X-ray beam with relatively low dose for suppression of X-ray exposure of the examinee "P" and the operator.

On the supporting plate 16, the X-ray generating unit translating device 24 and the X-ray detecting unit translating device 22 are provided. The X-ray generating unit translating device 24 and the X-ray detecting unit translating device 22 translate on guide rails 25 and 23 placed toward the rotational axis "A" so as to move the X-ray generating unit 20 and the X-ray detecting unit 18 in parallel, respectively. The distance between the breast "B" and the X-ray detecting unit 18 is changed according to the size of the breast "B" as an object to be inspected for adjustment of the image scaling factor, and thereby, the size of the image of the breast "B" can be adjusted. Further, when the breast "B" as the object is beyond the application range of the X-ray beam "C" and the imaging range of the X-ray detecting unit 18, the breast can be made within the imaging range by taking the distance between the breast "B" and the X-ray generating unit 20 larger to reduce the image scaling factor. Furthermore, in the case where the rotational shaft 26 supporting the supporting plate 16 is allowed to move in the vertical direction, the end part of the breast "B" can be imaged by moving the set of the X-ray generating unit 20 and the X-ray detecting unit 18 downward together to move the imaging region to the end part of the breast "B".

The obtained X-ray tomographic image is displayed on the image display unit 140 (FIG. 1). In a diagnosis using an x-ray tomographic image, the x-ray tomographic image is formed by using information on plural X-ray images, and thus, detectivity is high especially with respect to tumor masses. However, high-frequency information is deteriorated when the x-ray tomographic image is created by reconstructing the plural X-ray images, and thus, the detectivity is not high especially with respect to fine calcification. Therefore, in order to diagnose breast cancer, it is desirable to obtain an X-ray planar image that accurately shows the fine calcification in the second imaging mode.

Referring to FIG. 5, in order to obtain the X-ray planar image in the second imaging mode, when a doctor observes the X-ray tomographic image and designates a focus (tumor mass or calcified part) "F" to be carefully examined, the adjustment value computing unit 150 (FIG. 1) computes the imaging direction for obtaining the X-ray planar image such that the imaging direction may be substantially orthogonal to the plane "T" including the rotational axis "A" and the focus "F" based on the location of the designated focus "F".

For example, as shown in FIG. 5, in the case where the designated focus "F" is located at an angle α (degrees) clockwise with respect to the reference axis "S", the X-ray generating unit 20 and the X-ray detecting unit 18 are positioned such that the line connecting between the X-ray generating unit 20 and the X-ray detecting unit 18 is in the direction at an angle β=90°−α (degrees) counter-clockwise with respect to the reference axis "S".

In the second imaging mode, when the control unit 162 (FIG. 1) positions the X-ray generating unit 20 and the X-ray detecting unit 18 in the computed direction and allows the X-ray generating unit 20 to radiate an X-ray beam, the X-ray detecting unit 18 detects the X-ray planar image to output detection signals. The detection signals outputted from the X-ray detecting unit 18 are received by the image processing unit 120 (FIG. 1), and the image processing unit 120 generates planar image signals representing the X-ray planar image based on the detection signals. The obtained X-ray planar image is displayed on the image display unit 140 (FIG. 1) and used together with the X-ray tomographic image, and thereby, contributes to early recognition of breast cancer. Since it is not necessary to obtain a large number of X-ray planar images, in view of X-ray exposure, the dose of X-ray beam may be significantly high. By using a high-dose X-ray beam, a small calcified part can be clearly imaged and an accurate diagnosis can be made.

In the case where a developed automatic examination technique is used, the tumor mass or calcification required to be carefully examined can be automatically determined, and the X-ray generating unit 20 and the X-ray detecting unit 18 can be positioned in the imaging direction for obtaining an image in which the tumor mass or calcification can be clearly seen. However, a number of image of the tumor mass or calcification required for accurate diagnosis by the doctor is not always one, and the selection condition is not always a size of the tumor mass or calcification, and thus, the operation unit 161 (FIG. 1) to be used by the doctor for designating the subject of the examination according to need must be required. Further, it is preferable that the operation unit 161 may be used not only for designating the tumor mass or calcification as the subject of the examination but also for directly designating the imaging direction.

Figure 6:
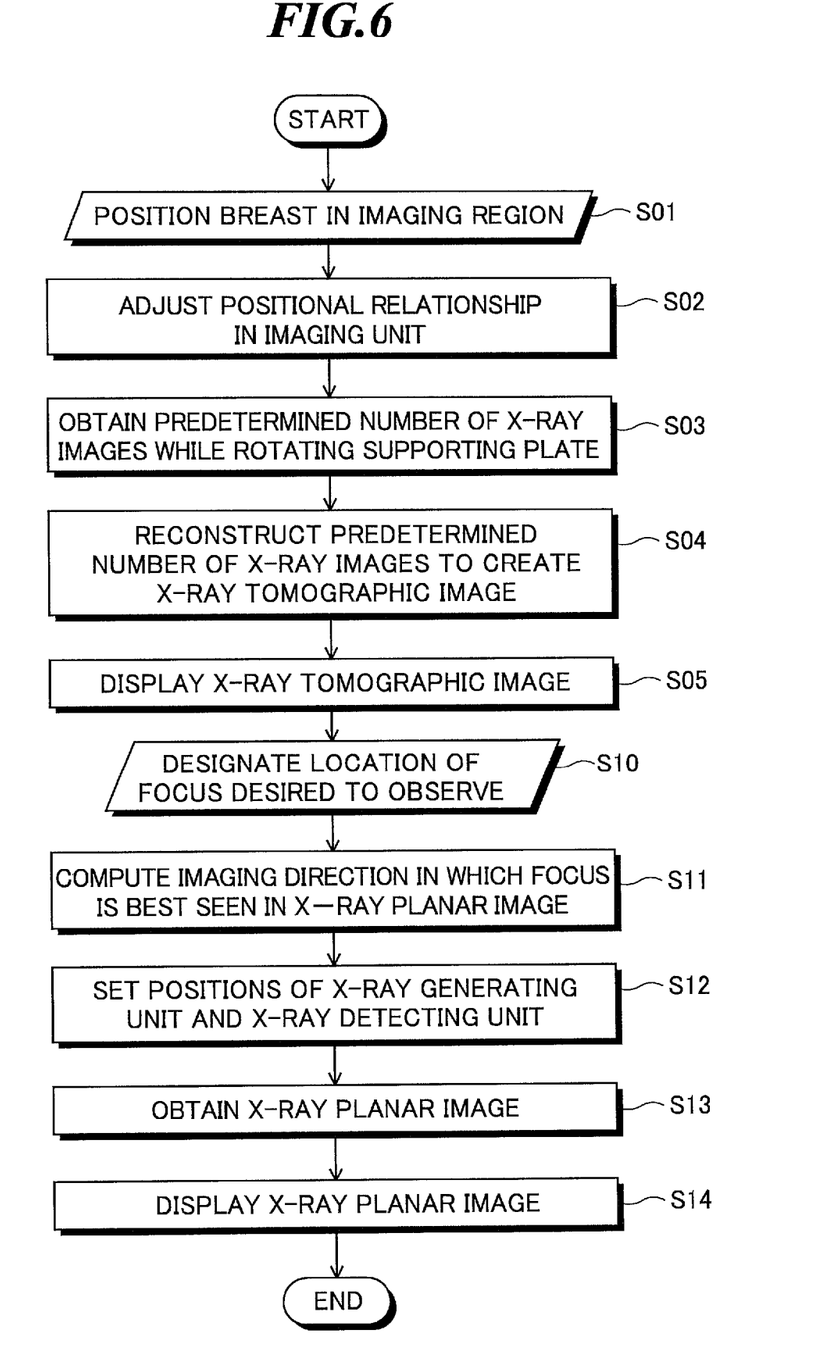
FIG. 6 is a flowchart showing a radiation imaging method to be used in the radiation imaging apparatus according to one embodiment of the present invention.

Next, a radiation imaging method to be used in the radiation imaging apparatus according to one embodiment of the present invention will be explained with reference to FIGS. 1-6. FIG. 6 is a flowchart showing a radiation imaging method to be used in the radiation imaging apparatus according to one embodiment of the present invention.

At step S01, when the examinee "P" mounts the table 12, lies face-down, and inserts the breast "B" into the opening 14 formed in the opening part of the table 12, the breast "B" passes through the opening 14 and is positioned in the imaging region between the X-ray generating unit 20 and the X-ray detecting unit 18. The opening 14 may be selected from among openings having sizes and shapes adapted to the respective breasts "B" having different sizes and shapes depending on examinees P. Further, it is preferable that the opening part is made of a material such as a silicon resin that deforms according to the breast shape. The examinee "P" is protected by a shielding member such that the parts other than the breast "B" are not exposed to the X-ray.

Then, the adjustment value computing unit 150 determines whether the range of the breast sufficient for diagnosis is within the imaging region or not. For this purpose, X-ray imaging with low dose is performed, and the image for review generating unit 127 supplies an image for review signal representing an image for review to the adjustment value computing unit 150. In place of X-ray imaging, optical imaging using a light source and a CCD camera may be performed for the determination based on an optical image of the breast "B".

The obtained image is used for determining whether the nipple as the lower boundary and the breast wall as the upper boundary are suitably within the imaging region or not. This determination is performed by the adjustment value computing unit 150 executing image analysis or the like, or may be performed by the operator. For this reason, the image for review is displayed on the image display unit 140 for the operator to observe.

In the determination, the location of the marker attached or applied to the surface of the breast "B" of the examinee "P" is confirmed in the image, and thereby, the proper imaging region can be recognized. Further, when the low-dose X-ray is used, the shadow of a costal bone or breast bone may be used as a marker. The determination result by the adjustment value computing unit 150 is outputted to the control unit 162.

If the control unit 162 determines that the range of the breast sufficient for diagnosis is not within the imaging region, at step S02, the control unit 162 adjusts the positional relationship in the imaging unit 110. The control unit 162 adjusts the relative position of the table 12 and the supporting plate 16 such that the imaging region is appropriate. The adjustment of the relative position of the table 12 and the supporting plate 16 may be made by moving at least one of the table 12 and the supporting plate 16.

Further, if the breast "B" is large and beyond the imaging region, X-ray images can be obtained while the supporting plate 16 for supporting the X-ray generating unit 20 and the X-ray detecting unit 18 is vertically shifted. For this purpose, the control unit 162 computes the amount of adjustment of relative position of the supporting plate 16 to the table 12 and the number of rotations of the supporting plate 16, and controls the respective parts to perform X-ray imaging while shifting them from the base to the end of the breast. Alternatively, as described above, the entire breast may be made within the imaging region by adjusting the distance between the rotational axis "A" and the X-ray generating unit 20 or X-ray detecting unit 18, i.e., the geometry.

It is preferable that the determination as to whether the range of the breast sufficient for diagnosis is within the imaging region or not and the adjustment of the relative position of the breast and the radiation imaging apparatus 100 are automatically performed by the radiation imaging apparatus 100 itself, however, the operator may perform determination and manual adjustment. For the operator to perform accurate determination and adjustment, in the image for review displayed on the image display unit 140, it is preferable that auxiliary indication such as scale indication is provided for assisting evaluation of the positional relationship between the nipple and/or breast wall and the boundary of the imaging region and computation of the amount of adjustment. Further, the operator may manually input the amount of adjustment by operating the operation unit 161.

If the control unit 162 determines that the range of the breast sufficient for diagnosis is within the imaging region, at step S03, the radiation imaging apparatus 100 performs X-ray imaging for obtaining an X-ray tomographic image in the first imaging mode. The control unit 162 controls the rotational driving device 28 to rotate the supporting plate 16 for supporting the X-ray generating unit 20 and the X-ray detecting unit 18, and supplies a trigger signal at each time when the supporting plate 16 rotates by a predetermined angle, and the X-ray generating unit 20 applies an X-ray beam C. The dose of the X-ray beam "C" is made relatively small for preventing exposure of the examinee P. The X-ray detecting unit 18 two-dimensionally detects the X-ray beam "C" applied by the X-ray generating unit 20 and transmitted through the breast "B" to output detection signals. The image signal generating unit 121 of the image processing unit 120 generates image signals representing a predetermined number of X-ray images necessary for obtaining a tomographic image based on the detection signals outputted from the X-ray detecting unit 18, to obtain the predetermined number of X-ray images. The image correcting unit 123 performs correction processing such as removing noise and reducing artifacts on the received image signals, and outputs the corrected image signals to the image reconstructing unit 125.

At step S04, the image reconstructing unit 125 reconstructs the predetermined number of X-ray images to create an X-ray tomographic image (CT image), and thereby, generates a tomographic image signal representing the X-ray tomographic image. At step S05, the image display unit 140 displays the X-ray tomographic image.

The doctor making a diagnosis can check the X-ray tomographic image displayed on the image display unit 140 and determine whether there is a tumor mass, calcified part, or the like in the breast or not. In the diagnosis using the X-ray tomographic image, the X-ray tomographic image is formed by using information of plural X-ray images, and thus, detectivity is high especially with respect to tumor masses. However, high-frequency information is deteriorated when the X-ray tomographic image is created by reconstructing the plural X-ray images, and thus, the detectivity is not high especially with respect to fine calcification. Therefore, in order to diagnose breast cancer, it is desirable to obtain an X-ray planar image that accurately shows the fine calcification in the second imaging mode.

In order to obtain the X-ray planar image, that accurately displays calcification necessary for the diagnosis, in the second imaging mode, at step S10, the doctor operates the operation unit 161 to designate the location of the focus desired to observe in the X-ray tomographic image. Alternatively, the adjustment value computing unit 150 may automatically determine the observation location based on the result of the evaluation of the X-ray tomographic image.

At step S11, the adjustment value computing unit 150 computes an imaging direction in which the focus is best seen when the focus at the designated location is observed in the X-ray planar image. It is desirable that the imaging direction is a direction substantially orthogonal to the plane including the rotational axis "A" and the designated focus location.

At step S12, when the adjustment value computing unit 150 outputs the computed imaging direction to the control unit 162, the control unit 162 controls the rotational driving device 28 according to the imaging direction. Thereby, the rotational driving device 28 rotates the supporting plate 16 for supporting the X-ray generating unit 20 and the X-ray detecting unit 18 around the rotational axis "A", and sets the positions of the X-ray generating unit 20 and the X-ray detecting unit 18.

At step S13, the control unit 162 outputs a trigger signal to the x-ray generating unit 20 so that the x-ray generating unit 20 generates an X-ray beam with relatively high dose. The X-ray detecting unit 18 two-dimensionally detects the X-ray transmitted through the breast "B" to output detection signals, the image processing unit 120 generates a planar image signal based on the detection signals, and thereby, obtains an x-ray planar image. Since the imaging is performed substantially orthogonally to the plane including the rotational axis "A" and the designated focus location, the X-ray planar image obtained in the second imaging mode most clearly shows the X-ray absorption condition of the focus.

At step S14, the image display unit 140 displays the X-ray planar image based on the planar image signal generated in the image processing unit 120. The image display unit 140 can display the X-ray tomographic image obtained at step S03 and the X-ray planar image obtained at step S13 side by side or one by one.

Then, the doctor observes the X-ray tomographic image and the X-ray planar image selectively displayed on the image display unit 140, and performs a breast cancer examination. A tumor mass is clearly displayed in the X-ray tomographic image and calcification is clearly displayed in the X-ray planar image, and therefore, a more accurate diagnosis can be made by using both images than in the conventional case.

Figure 7:
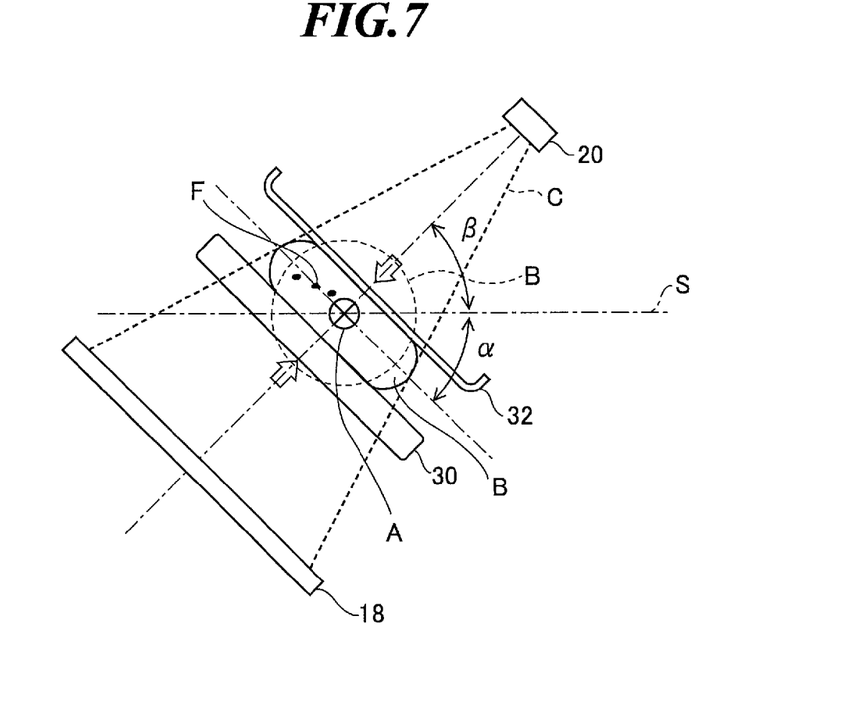
FIG. 7 is a plan view showing the case of using compression plates in the radiation imaging apparatus according to one embodiment of the present invention.

FIG. 7 is a plan view showing the case of using compression plates in the radiation imaging apparatus according to one embodiment of the present invention. A pair of compression plates 30 and 32 are formed of plastics or the like having a low X-ray absorption factor, and positioned to face each other along a line connecting between the X-ray generating unit 20 and the X-ray detecting unit 18 (in the imaging direction) when sandwiching the breast "B". In the second imagine mode, the breast "B" is compressed by the compression plates 30 and 32 along the X-ray application direction and imaging is performed while the thickness of the breast "B" is made thin and uniform and the focus "F" is fixed, and a clear X-ray planar image can be obtained. Thereby, observation of the focus "F" becomes easier.

As shown in FIG. 7, in the case where the focus "F" designated based on the observation of the X-ray tomographic image is located at the angle α (degrees) clockwise with respect to the reference axis "S", it is preferable that the line connecting between the X-ray generating unit 20 and the X-ray detecting unit 18 is in the direction at an angle β=90°−α (degrees) counter-clockwise with respect to the reference axis "S". According to the positioning, when the breast "B" is sandwiched between the compression plates 30 and 32, the focus "F" exists substantially in the middle of the thickness of the breast "B" and at the location farthest from the rotational axis "A". Therefore, the image of the focus "F" is formed to be best seen and the focus "F" can be accurately observed.

Figure 8:
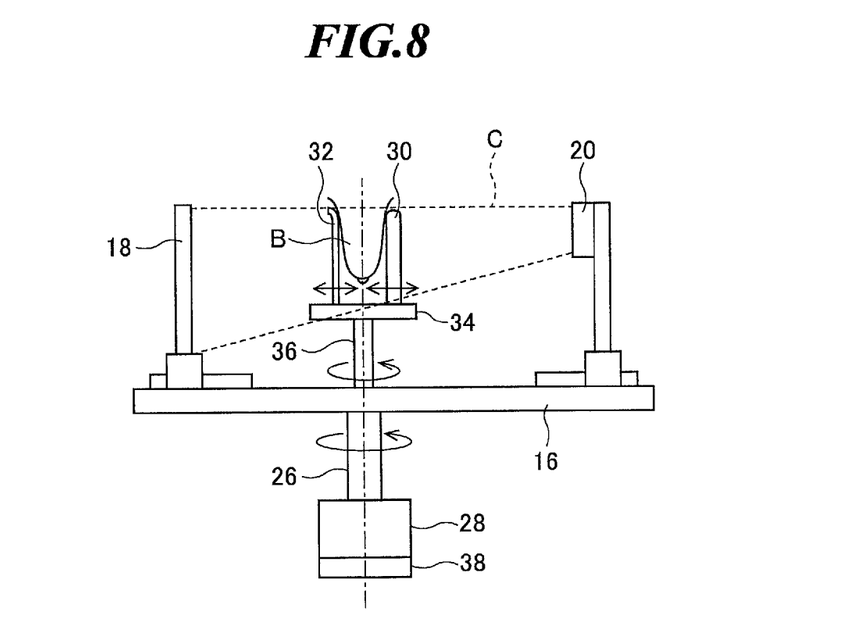
FIG. 8 is a side view showing the case of using compression plates in the radiation imaging apparatus according to one embodiment of the present invention.

FIG. 8 is a side view showing the case of using compression plates in the radiation imaging apparatus according to one embodiment of the present invention. As shown in FIG. 8, a compression plate supporting plate 34 for supporting the compression plates 30 and 32 is connected to a rotational shaft 36. The rotational shaft 36 has a coaxial structure with respect to the rotational shaft 26 connected to the supporting plate 16 for supporting the X-ray generating unit 20 and the X-ray detecting unit 18. The compression plate rotating device 38 provided below the rotational driving device 28 rotates the rotational shaft 36 to adjust the direction of the compression plates 30 and 32. Further, the gap between the compression plates 30 and 32 is adjusted by the compression plate translating device 185 (FIG. 1) so that the compression force on the breast "B" is controlled.

On the other hand, when an X-ray tomographic image is obtained in the first imaging mode, since the compression plates 30 and 32 attenuates X-ray energy, the compression plates 30 and 32 are required to be retracted from the imaging region of the X-ray beam C. Accordingly, the control unit 162 (FIG. 1) controls the compression plate control unit 180 (FIG. 1) such that the pair of compression plates 30 and 32 are retracted from the imaging region in the first imaging mode, and controls the compression plate control unit 180 such that the pair of compression plates 30 and 32 compress the breast along the imaging direction in the second imaging mode.

Figure 9A:
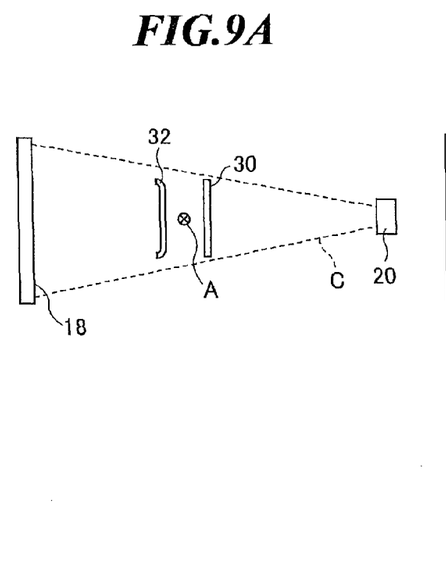
FIGS. 9A and 9B are plan views for explanation of the first example of a method of retracting the compression plates.
Figure 9B:
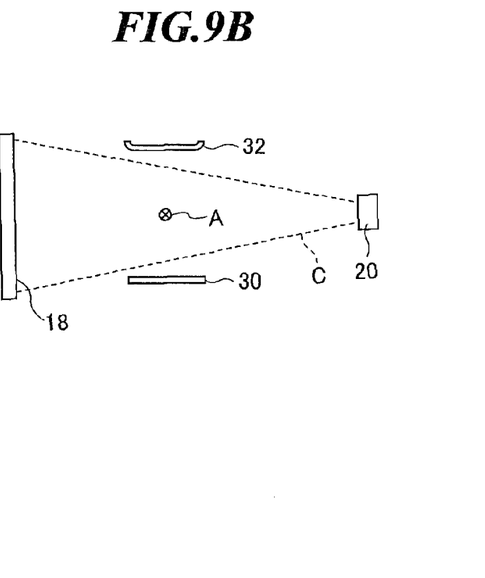

FIGS. 9A and 9B are plan views for explanation of the first example of a method of retracting the compression plate. FIG. 9A is a plan view of the compression plates when the compression plates are compressing the breast, and FIG. 9B is a plan view of the compression plates when the compression plates are retracted from the imaging region.

As shown in FIG. 9A, when an X-ray planar image is obtained in the second imaging mode, the X-ray generating unit 20 and the X-ray detecting unit 18 are fixed in a predetermined imaging direction, and the compression plates 30 and 32 are positioned on the line connecting between the X-ray generating unit 20 and the X-ray detecting unit 18 and sandwich the breast. On the other hand, as shown in FIG. 9B, when an X-ray tomographic image is obtained in the first imaging mode, the X-ray generating unit 20 and the X-ray detecting unit 18 perform X-ray imaging while rotating around the breast, and the compression plates 30 and 32 are positioned to face each other along a direction orthogonal to the line connecting between the X-ray generating unit 20 and the X-ray detecting unit 18 (the imaging direction) for avoiding the X-ray beam "C" entering the breast "B", and retracted to the outside of the X-ray beam "C".

The retracted compression plates 30 and 32 are necessary to rotate with the rotation of the X-ray generating unit 20 and the X-ray detecting unit 18, however, the compression plate supporting plate 34 as shown in FIG. 8 may be fixed substantially orthogonal to the supporting plate 16 and both of them may be rotated by the rotational driving device 28. In the second imaging mode, when the compression plates 30 and 32 sandwich the breast, the compression plate supporting plate 34 may be fixed in the same direction as that of the supporting plate 16, and both of them may be rotated together, and therefore, the compression plate rotating device 38 may rotate the compression plate supporting plate 34 by 90° relative to the supporting plate 16. Of course, the compression plate rotating device 38 may independently rotate the compression plates 30 and 32 at the same speed as that of the supporting plate 16.

Figure 10A:
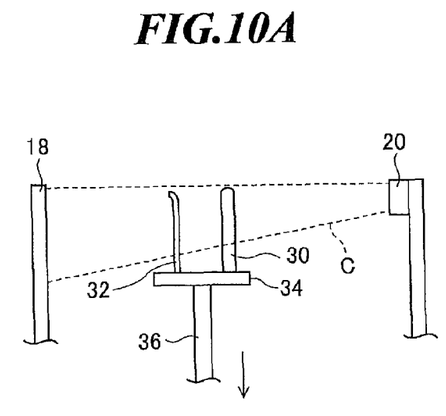
FIGS. 10A and 10B are side views for explanation of the second example of the method of retracting the compression plates.
Figure 10B:
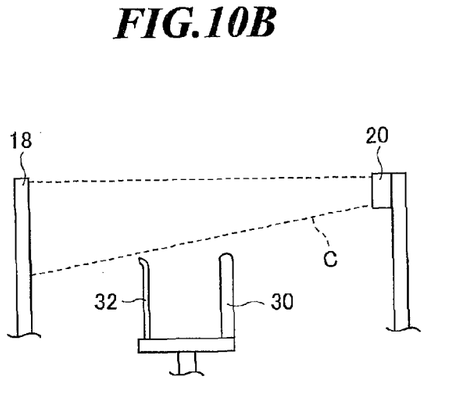

FIGS. 10A and 10B are side views for explanation of the second example of the method of retracting the compression plates. FIG. 10A is a side view of the compression plates when the compression plates are compressing the breast, and FIG. 10B is a side view of the compression plates when the plates are retracted from the imaging region. As shown in FIG. 10A, when an X-ray planar image is obtained in the second imaging mode, the compression plates 30 and 32 are pushed upward close to the upper edge of the X-ray beam "C" by the compression plate retracting device 183 (FIG. 1) to be positioned to sandwich the breast.

On the other hand, as shown in FIG. 10B, when an X-ray tomographic image is obtained in the first imaging mode, the compression plates 30 and 32 are moved below the lower end of the X-ray beam "C" by the compression plate retracting device 183 and retracted from the X-ray beam "C". The retracted compression plates 30 and 32 may rotate together or stop while the X-ray generating unit 20 and the X-ray detecting unit 18 rotate. The method of retracting the compression plates is not limited to the above-mentioned methods, but there are, for example, a method of tilting the compression plates for avoiding the imaging region, and so on.

The invention claimed is:

1. A radiation imaging apparatus comprising:
    a table formed with an opening for allowing a breast of an examinee to pass through when the examinee lies down on the table;
    a radiation generating unit for applying a radiation beam to the breast passing through the opening of said table;
    a radiation detecting unit for detecting the radiation beam applied by said radiation generating unit and transmitted through the breast to output detection signal;

a supporting plate for supporting said radiation generating unit and said radiation detecting unit such that said radiation generating unit and said radiation detecting unit are rotatable around a rotational axis while facing each other with the breast in between, said rotational axis being substantially orthogonal to said table and passing through said opening;

a rotational driving device for rotating said supporting plate around the rotational axis;

an image processing unit for generating image signals representing a predetermined number of radiation images based on the detection signal outputted from said radiation detecting unit at each time when said radiation generating unit and said radiation detecting unit rotate by a predetermined angle and generating a tomographic image signal representing a radiation tomographic image by reconstructing the predetermined number of radiation images in a first imaging mode for obtaining the radiation tomographic image, and for generating a planar image signal representing a radiation planar image based on the detection signal outputted from said radiation detecting unit in a second imaging mode for obtaining the radiation planar image;

a computing unit for computing an imaging direction for obtaining the radiation planar image in the second imaging mode such that the imaging direction is substantially orthogonal to a plane including said rotational axis and a location designated in the radiation tomographic image obtained in the first imaging mode;

a control unit for controlling said rotational driving device and said radiation generating unit to perform imaging at each time when said radiation generating unit and said radiation detecting unit rotate by the predetermined angle so as to obtain the radiation tomographic image in the first imaging mode, and controlling said rotational driving device and said radiation generating unit to perform imaging in the imaging direction computed by said computing unit so as to obtain the radiation planar image in the second imaging mode; and an image display unit for selectively displaying at least one of the radiation tomographic image obtained in the first imaging mode and the radiation planar image obtained in the second imaging mode.

2. The radiation imaging apparatus according to claim 1, further comprising:
a pair of compression plates for compressing the breast passing through the opening of said table from both sides in the second imaging mode.

3. The radiation imaging apparatus according to claim 2, further comprising:
a compression plate control unit for adjusting positions and directions of said pair of compression plates;
wherein said control unit controls said compression plate control unit such that said pair of compression plates are retracted from an imaging region between said radiation generating unit and said radiation detecting unit in the first imaging mode, and controls said compression plate control unit such that said pair of compression plates compress the breast from both sides along the imaging direction in the second imaging mode.

4. The radiation imaging apparatus according to claim 1, wherein said control unit sets a radiation dose to be used in the second imaging mode higher than that used in the first mode.

5. The radiation imaging apparatus according to claim 1, wherein said control unit changes at least one of a wavelength and a dose of radiation by changing at least one of a tubular voltage, a target, and a filter of said radiation generating unit to be used in the second imaging mode from that used in the first imaging mode.

6. The radiation imaging apparatus according to claim 1, wherein said control unit sets pixel density of said radiation detecting unit to be used in the second imaging mode higher than that used in the first imaging mode.

7. A radiation imaging method to be used in a radiation imaging apparatus including a table formed with an opening for allowing a breast of an examinee to pass through when the examinee lies down on the table, a radiation generating unit for applying a radiation beam to the breast passing through the opening of said table, a radiation detecting unit for detecting the radiation beam applied by said radiation generating unit and transmitted through the breast to output detection signal, a supporting plate for supporting said radiation generating unit and said radiation detecting unit such that said radiation generating unit and said radiation detecting unit are rotatable around a rotational axis while facing the breast in between, said rotational axis being substantially orthogonal to said table and passing through said opening, and a rotational driving device for rotating said supporting plate around the rotational axis, said method comprising the steps of:

(a) controlling said rotational driving device and said radiation generating unit to perform imaging at each time when said radiation generating unit and said radiation detecting unit rotate by a predetermined angle so as to obtain a radiation tomographic image;

(b) generating image signals representing a predetermined number of radiation images based on the detection signal outputted from said radiation detecting unit at each time when said radiation generating unit and said radiation detecting unit rotate by the predetermined angle, and generating a tomographic image signal representing a radiation tomographic image by reconstructing the predetermined number of radiation images;

(c) computing an imaging direction for obtaining a radiation planar image such that the imaging direction is substantially orthogonal to a plane including said rotational axis and a location designated in the radiation tomographic image obtained at step (b);

(d) controlling said rotational driving device and said radiation generating unit to perform imaging in the imaging direction computed at step (c) so as to obtain the radiation planar image;

(e) generating a planar image signal representing the radiation planar image based on the detection signal outputted from said radiation detecting unit; and (f) selectively displaying at least one of the radiation tomographic image obtained at step (b) and the radiation planar image obtained at step (e).

8. The radiation imaging method according to claim 7, wherein:
step (a) includes controlling a compression plate control unit such that a pair of compression plates are retracted from an imaging region between said radiation generating unit and said radiation detecting unit; and
step (d) includes controlling said compression plate control unit such that said pair of compression plates compress the breast from both sides along the imaging direction.

9. The radiation imaging method according to claim 7, wherein step (d) includes setting a radiation dose to be used larger than that used at step (a).

10. The radiation imaging method according to claim 7, wherein step (d) includes changing at least one of a wavelength and a dose of radiation by changing at least one of a tubular voltage, a target, and a filter to be used from that used at step (a).

11. The radiation imaging method according to claim 7, wherein step (d) includes setting pixel density of said radiation detecting unit to be used higher than that used at step (a).

* * * * *